United States Patent
Lavagna et al.

(10) Patent No.: US 8,952,159 B2
(45) Date of Patent: Feb. 10, 2015

(54) METHOD FOR THE PRODUCTION OF AMORPHOUS RIFAXIMIN

(76) Inventors: Silvio Massimo Lavagna, Rome (IT); Daniela Secci, Rome (IT); Franco Padella, Anguillara Sabazia (IT)

( * ) Notice: Subject to any disclaimer, the term of this patent is extended or adjusted under 35 U.S.C. 154(b) by 304 days.

(21) Appl. No.: 13/519,340

(22) PCT Filed: Dec. 27, 2010

(86) PCT No.: PCT/IB2010/056080
§ 371 (c)(1),
(2), (4) Date: Jun. 27, 2012

(87) PCT Pub. No.: WO2011/080691
PCT Pub. Date: Jul. 7, 2011

(65) Prior Publication Data
US 2012/0289532 A1    Nov. 15, 2012

(30) Foreign Application Priority Data

Dec. 28, 2009 (IT) .............................. RM2009A0686
Apr. 2, 2010 (IT) .............................. RM2010A0157

(51) Int. Cl.
*C07D 491/00* (2006.01)
*C07D 491/22* (2006.01)
*C07D 498/22* (2006.01)

(52) U.S. Cl.
CPC .................................. *C07D 498/22* (2013.01)

USPC ............................................. 546/40; 514/279

(58) Field of Classification Search
CPC .............................. C07D 471/22; C07D 491/22
USPC ............................................. 546/40; 514/279
See application file for complete search history.

(56) References Cited

U.S. PATENT DOCUMENTS

| | | |
|---|---|---|
| 2009/0082558 A1 | 3/2009 | Kothakonda et al. |
| 2009/0312357 A1 | 12/2009 | Rao et al. |
| 2010/0137580 A1 | 6/2010 | Vecchio et al. |
| 2010/0239664 A1 | 9/2010 | Gushurst et al. |
| 2011/0105550 A1 | 5/2011 | Gushurst et al. |

FOREIGN PATENT DOCUMENTS

| | | |
|---|---|---|
| WO | 2008/035109 | 3/2008 |
| WO | 2008/155728 | 12/2008 |
| WO | 2009/108730 | 9/2009 |

OTHER PUBLICATIONS

Diederen, International Search Report for PCT/IB2010/056080, all pages, mailed May 27, 2011.

*Primary Examiner* — John Mabry
(74) *Attorney, Agent, or Firm* — Nixon & Vanderhye PC

(57) ABSTRACT

The present invention relates to a new amorphous form of rifaximin and to methods for the preparation thereof by means of high energy milling or Spray drying. The present invention further relates to a new amorphous form for use as medicament and to the pharmaceutical compositions composing it.

16 Claims, 14 Drawing Sheets

METHOD FOR THE PRODUCTION OF AMORPHOUS RIFAXIMIN

Figure 1:
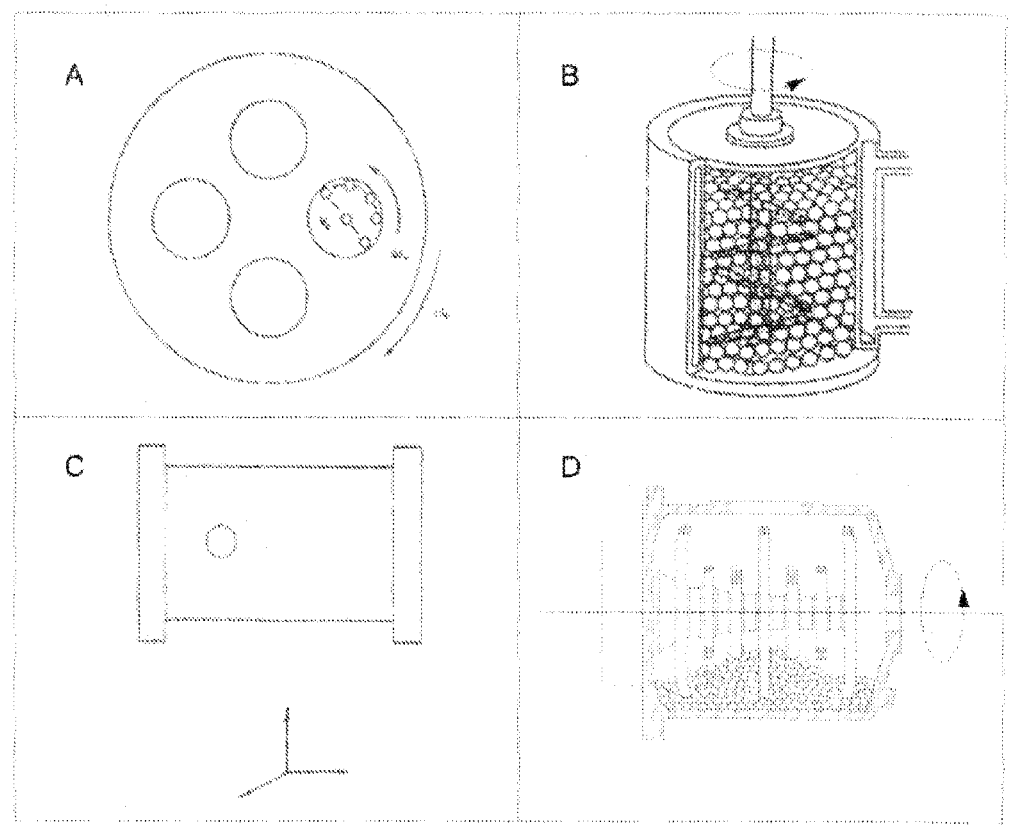

This application is the U.S. national phase of International Application No. PCT/IB2010/056080, filed 27 Dec. 2010, which designated the U.S. and claims priority to IT RM2009A000686 filed 28 Dec. 2009 and IT RM2010A000157 filed 2 Apr. 2010; the entire contents of each of which are hereby incorporated by reference.

The present invention relates to a new amorphous form of rifaximin and to methods for the production thereof by means of high energy milling or Spray drying. The present invention also relates to the new amorphous form for use as a medicament and to the pharmaceutical compositions comprising it.

STATE OF PRIOR ART

The phenomenon of polymorphism in chemistry is generated by the possibility that the same molecule organizes in different (polymorphic) crystals, crystallizes with solvent molecules (hydrates and solvates) or solidifies without periodicity (amorphous). The different crystalline or amorphous phases, even if they contain the same active molecule, can have even very different chemical, physical and mechanical properties with huge consequences upon the use thereof as active principles. In particular different solid forms show different chemical activities against other substances, which explicates with particular evidence in case of solvent or dispersing agents. Furthermore, the stability of the several forms can have very serious consequences upon maintaining the wished properties, such as the therapeutic efficiency in case of a molecule used as drug.

Rifamicyns are a known family of antibiotics produced by microrganisms, thereto 4 substances belong, produced in a semi-synthetic way, equipped with antibacterial activity and currently in commerce: rifaximin, rifamycin SV, rifampicyn and rifapentine. In particular, rifaximin is used in treating diarrhoea caused by the bacterium *E. Coli* both in adults and children and in other pathologies.

In the European patent EP1676848B1 three crystalline polymorphous forms of rifaximin, called alfa, beta and gamma, have been described and the differences among these three forms have been shown, in terms of water content and structural order, highlighted by different diffractograms of X rays. These forms are stated to be interconvertible therebetween by means of solubilization and recrystallization and a specific form can be obtained depending, among other things, upon the drying level of the powder itself. The gamma form described in the same patent EP1676848B1 appears with a low crystallinity value in a partially amorphous form. This gamma form can convert into the other crystalline polymorphous forms. When it appears in spontaneous form, the tendency to change form represents a disadvantage for a compound used as pharmaceutical active principle therefor it is a fundamental requirement, the stability in a specific polymorphous form.

The European patent application EP1698630 describes other two crystalline forms (called δ, ε). These forms are obtained with the same method type described in the patent EP1676848B1.

In the patent applications US2009/0082558A1 and WO/2008/155728 the obtaining of amorphous forms of rifaximin by means of precipitation in presence of proper agents is described. The advantage of both described methodologies consists in obtaining amorphous forms of rifaximin passing through a process stage providing to treat an already precipitated product by means of a new dissolution and subsequent reprecipitation (and consequent washing and drying). Furthermore, a comparative analysis performed on the XRD diffraction spectra reported in US2009/0082558A1 and in WO/2008/155728 shows that the obtained forms of rifaximin have a different level of structural disorder, as it can be deduced from a different relationship between the areas of the two characteristic halos of the disordered form in the two different cases. The specific amorphous forms obtained from these processes are strongly depending upon the used solvent agents, additives and antisolvents.

In the International patent applications WO92/00302 an amorphous form of rifaximin is described, substantially defined by an X-ray diffraction spectrum with a first diffraction halo at 7.3 degrees in 2θ and a second diffraction halo between 11.3-17.8 degrees in 2θ (radiation Cu $K_\alpha$). In the International patent application WO2009/108730, apart from other polymorphous forms, amorphous forms of rifaximin are described, obtained according to different modes having diffraction patterns characterized by two diffraction halos in the ranges 5.1-10.1 (maximum at 7.3) and 11.3-17.8 (maximum at 15.8) degrees in 2θ (radiation Cu $K_\alpha$).

Therefore, in the art the need was felt for proposing new amorphous forms of rifaximin and methods for the preparation thereof, not showing the disadvantages described in the known art.

SUMMARY OF THE INVENTION

In a wholly surprisingly way the inventors have succeeded in obtaining a new amorphous form of stable and pharmaceutically active rifaximin, different from other amorphous forms known up to now, with a maximum solubility measurable in water and a kinetics of solubization in water higher than other amorphous and crystalline forms of rifaximin known to the state of art. The higher solubility of this amorphous form is an advantage for all pharmaceutical applications as a high solubility value enhances the drug bioavailability; the higher solubility kinetics enhances the speed thereof therewith such drug reaches the effective concentrations.

The object of the present invention is a rifaximin in amorphous form characterized by an X-ray diffraction spectrum showing a single diffraction halo in the whole explored angular range and absence of peaks proper to crystalline forms. Such halo is positioned in the range 7.7-23.2 $nm^{-1}$ in Q units ($Q=4\pi sen\theta/\lambda$ is the definition for the scattering vector, which is an invariant unit with respect to the wavelength of the used X radiation) with a maximum positioned in the range 11.3-16.5+/−0.25 $nm^{-1}$ in Q units.

A second object of the present invention is a pharmaceutical composition comprising the rifaximin in amorphous form of the present invention and one or more excipients and/or one or more pharmaceutically acceptable carriers. A third object of the present description is a method for producing rifaximin in amorphous form comprising the steps of:

a) prearranging said rifaximin in powder form; and
b) subjecting said powder to a plurality of mechanical impacts with one or more milling bodies so that an integral energy density (also called dose) equal to at least 50 kJ/g is transferred, said integral energy density being so as to make said rifaximin assuming an amorphous state.

A fourth object of the present description is a method for preparing rifaximin in amorphous form comprising a passage wherein a rifaximin solution in one or more organic solvents is subjected to a spray-drying treatment in an atomiser. The advantages, the features and the using modes of the present invention will result evident from the following detailed description of some embodiments, shown by way of example and not with limitative purpose.

DETAILED DESCRIPTION OF THE FIGURES

FIG. 1. Principle schemes of some apparatuses for the processes of High Energy Ball Milling (HEBM).

In the figures four different typologies of high energy mills are illustrated: planet (Frisch type) (scheme A), attritor (scheme B), with oscillation (Spex 8000 type) (scheme C), and with central rotor (Symoloyer type) (scheme D). In the present invention apparatuses of planet type, with oscillation and with plates have been used, in the last case the jar is filled up with concentric rings and a central plate. The geometry of the used jars are the following ones:

Spex (scheme C). Cylindrical jar made of steel with outer height of 63 mm (excluding the cover), outer diameter 51 mm, useful height 57.5 mm and useful diameter 38 mm. In some experiments such jar has been accessorized with teflon jacket, so as to leave a useful chamber with cylindrical shape with height 57 mm and diameter 28.5 mm. An experiment has been performed with jar worked inside like an egg, so as not to have square edges inside. The amounts of useful volume are maximum height 57 mm and diameter 38 mm.

Fritsch (scheme A). Jar made of steel with outer diameter of 98 mm and diameter of the useful volume of 75 mm. Outer height 71 mm and height of the useful volume 55 mm.

Plate mill. Cylindrical jar made of steel equipped with a ring and a central body, made of steel too. The jar has a maximum outer diameter of 152 mm and outer height of 54.5 mm. The amounts of useful volume are 140 mm e 49.5 mm, respectively. The ring has height 45.5 mm, outer diameter 120 mm and inner diameter of 94 mm. The central body has a height of 45.5 mm and a diameter of 75 mm.

The geometry of a ZOZ Symoloyer mill (scheme D) consists in a jar with cylindrical shape and volume higher or equal to 2 liters. The marbles fill up the jar for a maximum volume not higher than 50% of the total volume. A rotor, which placed in rotation at speeds even higher than 1000 revolutions per minute imposes to the marbles a free motion (cataracting motion) and the subsequent impact against the walls.

Figure 2:
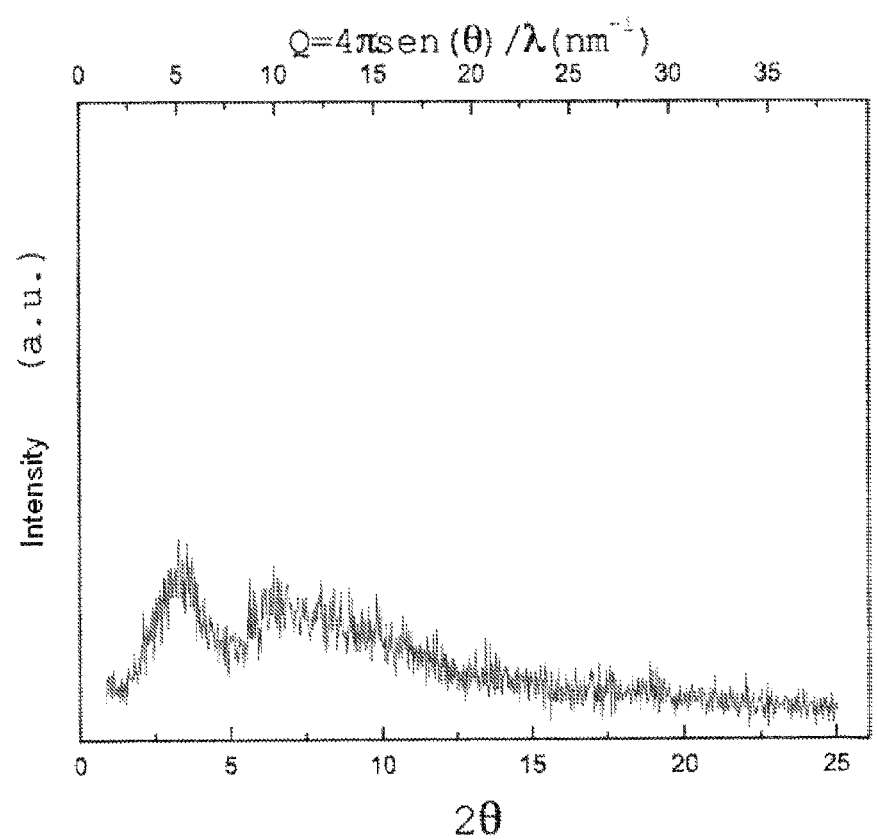

FIG. 2. X-ray diffraction spectrum (XRD) of the amorphous form of rifaximin obtained by means of the method described in the example 1.

Figure 3:
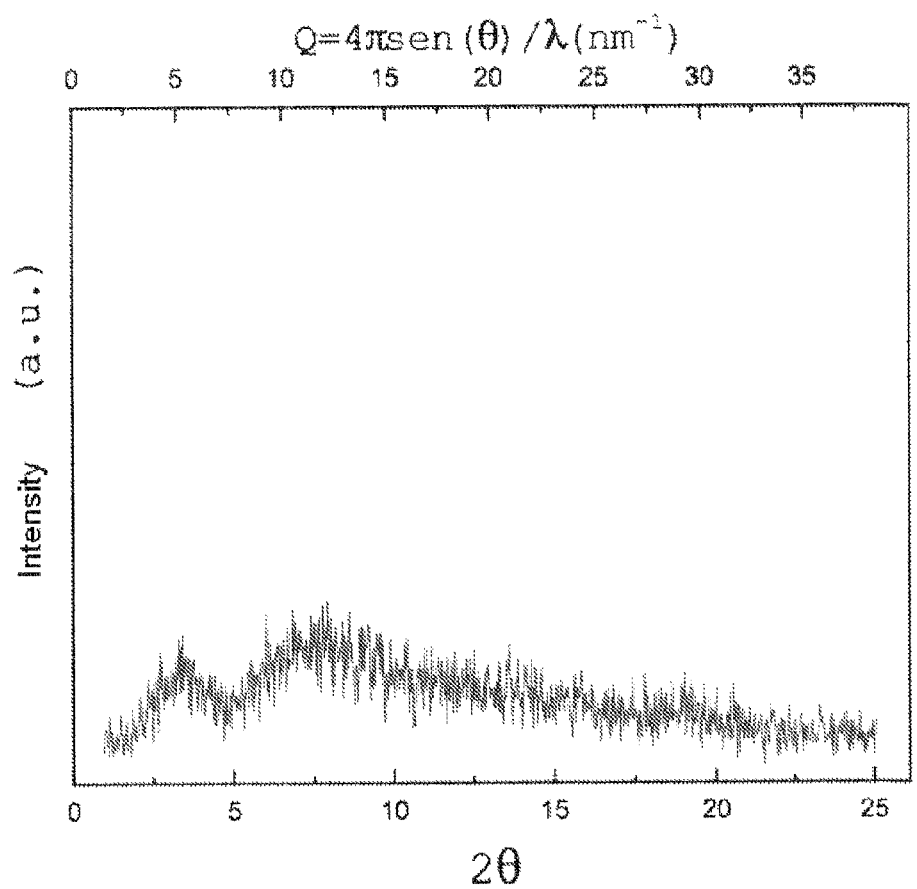

FIG. 3: X-ray diffraction spectrum (XRD) of the amorphous form of rifaximin obtained by means of the method described in the example 2.

Figure 4:
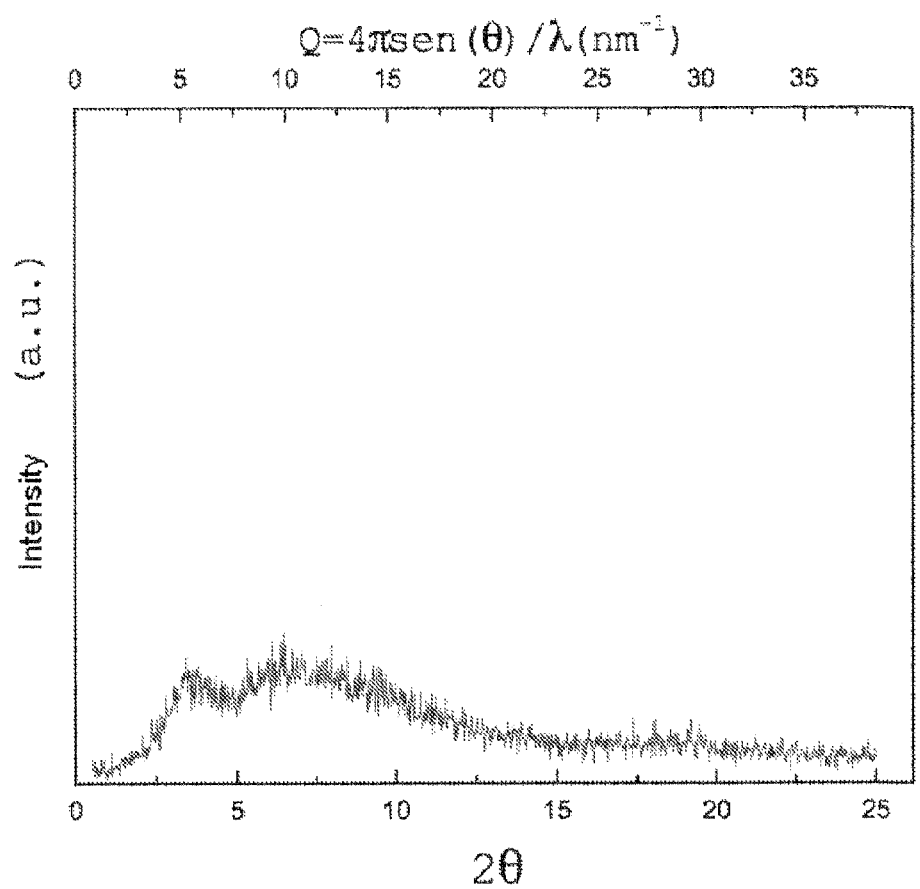

FIG. 4: X-ray diffraction spectrum (XRD) of the amorphous form of rifaximin obtained by means of the method described in the example 3.

Figure 5:
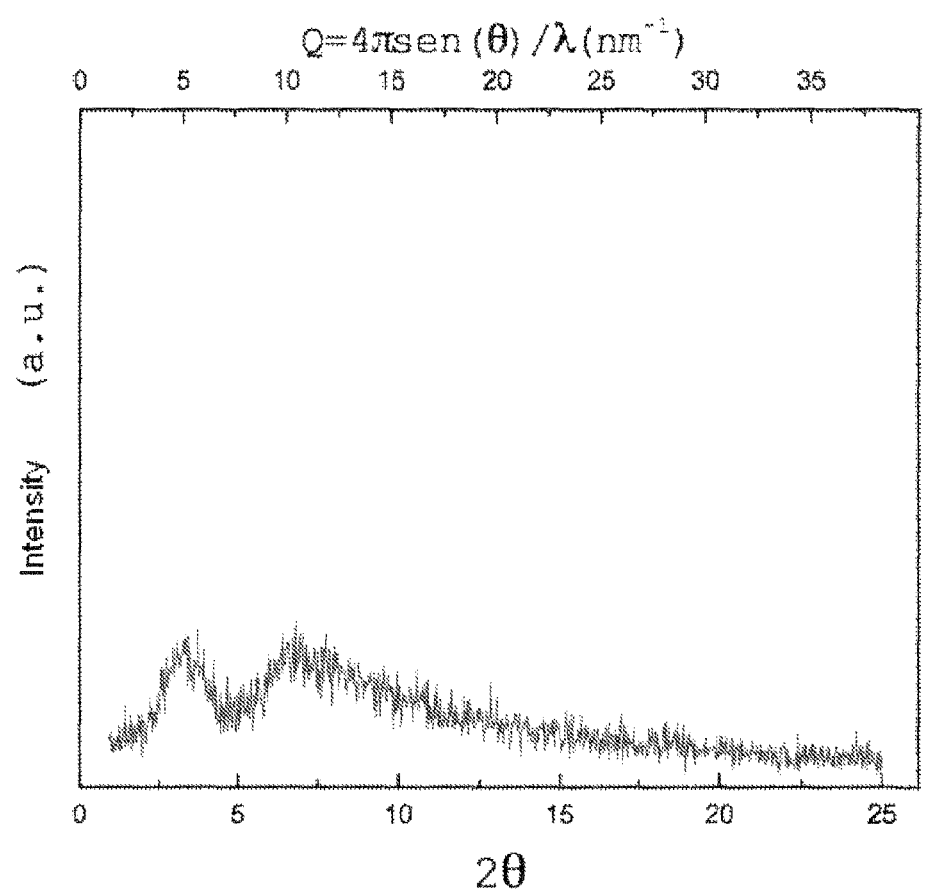

FIG. 5: X-ray diffraction spectrum (XRD) of the amorphous form of rifaximin obtained by means of the method described in the example 4.

Figure 6:
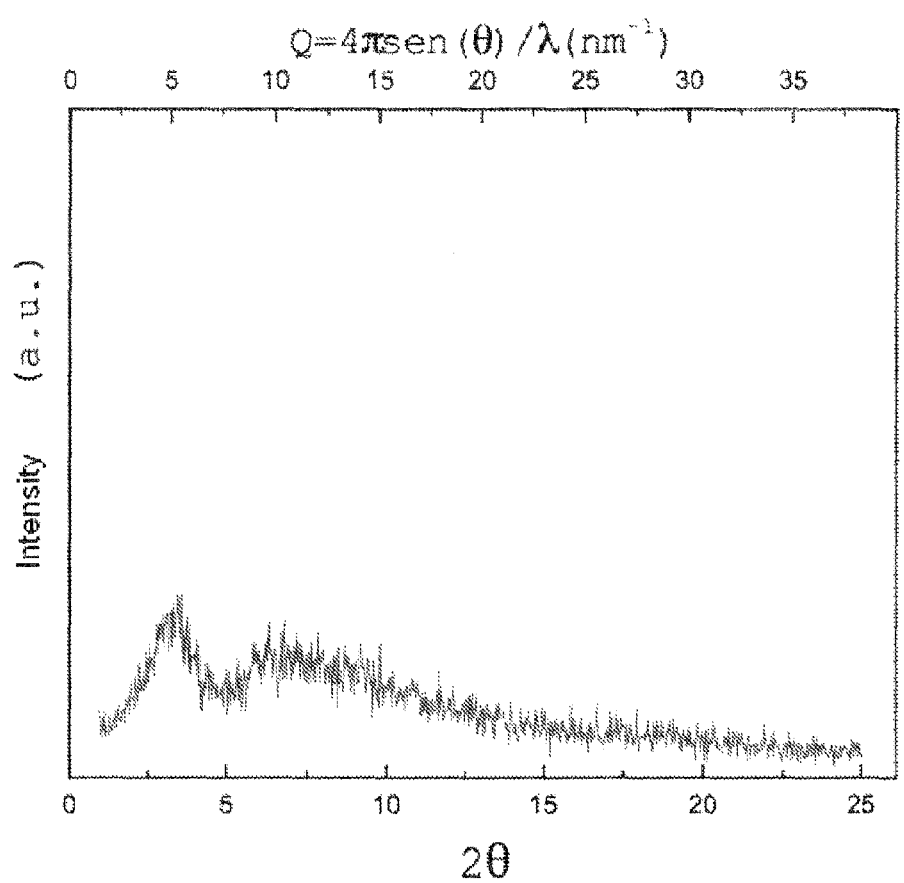

FIG. 6: X-ray diffraction spectrum (XRD) of the amorphous form of rifaximin obtained by means of the method described in the example 5.

Figure 7:
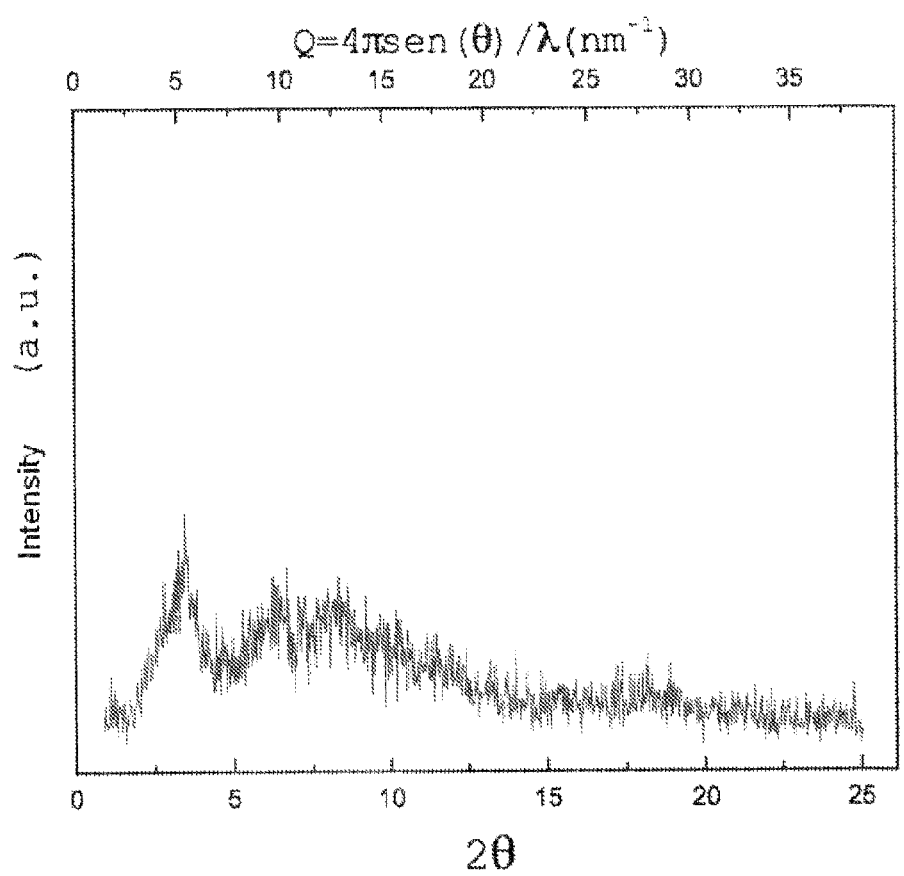

FIG. 7: X-ray diffraction spectrum (XRD) of the amorphous form of rifaximin obtained by means of the method described in the example 6.

Figure 8:
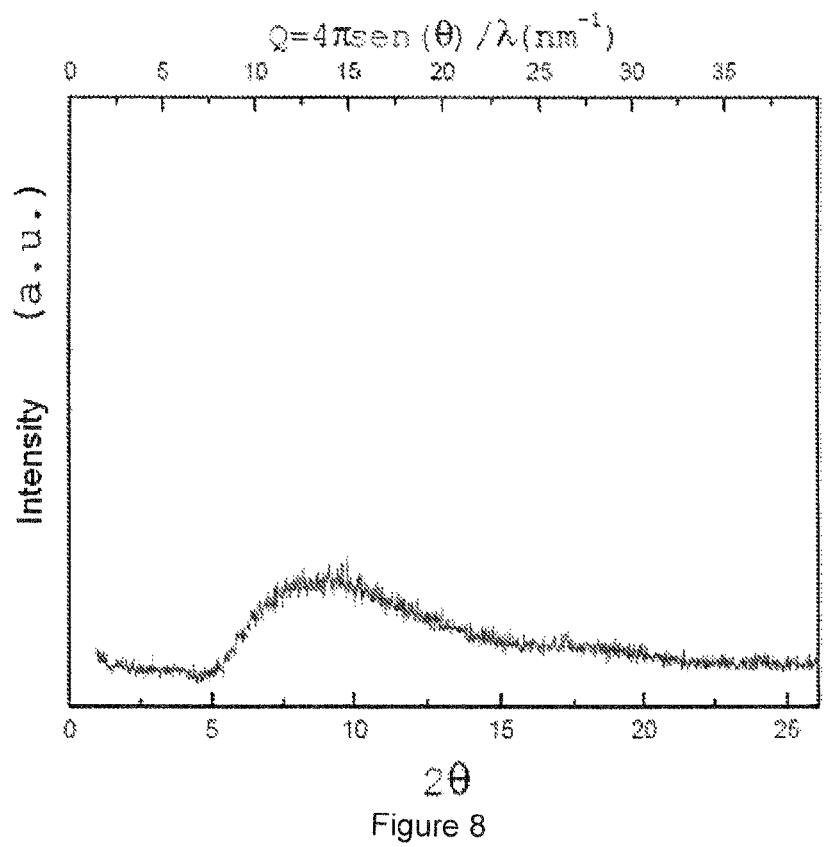

FIG. 8. X-ray diffraction spectrum (XRD) of the amorphous form of rifaximin obtained by means of the method described in the example 7. A single halo positioned in the range 7.7-23.2 $nm^{-1}$ and maximum at $\approx$11.5 $nm^{-1}$ in Q units is pointed out.

Figure 9:
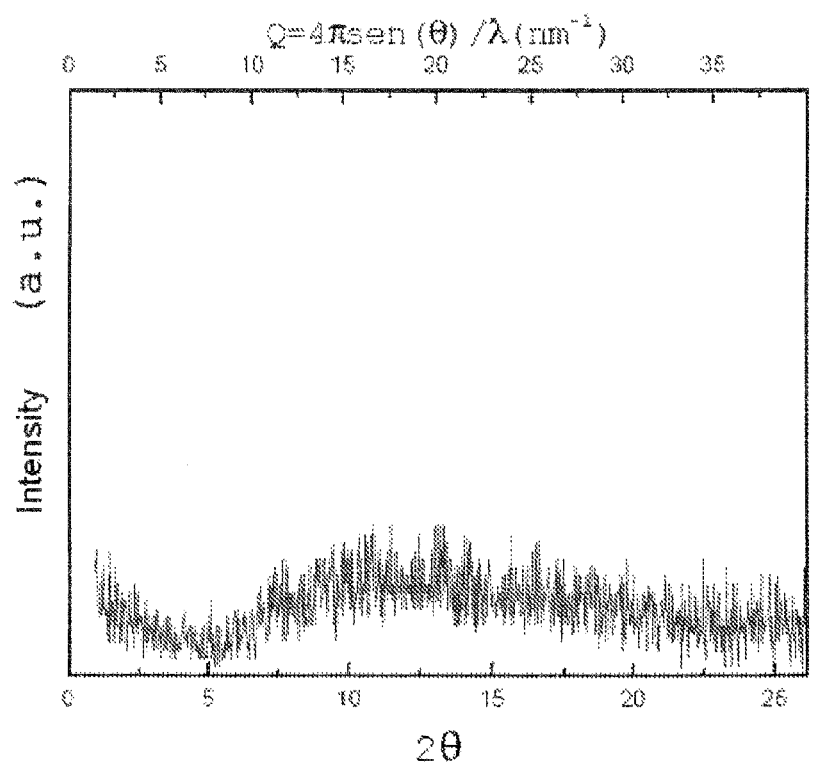

FIG. 9. X-ray diffraction spectrum (XRD) of the amorphous form of rifaximin obtained by means of the method described in the example 8. A single halo in the range 7.7-23.2 $nm^{-1}$ with maximum positioned at $\approx$16.3 $nm^{-1}$ in Q units is pointed out.

Figure 10:
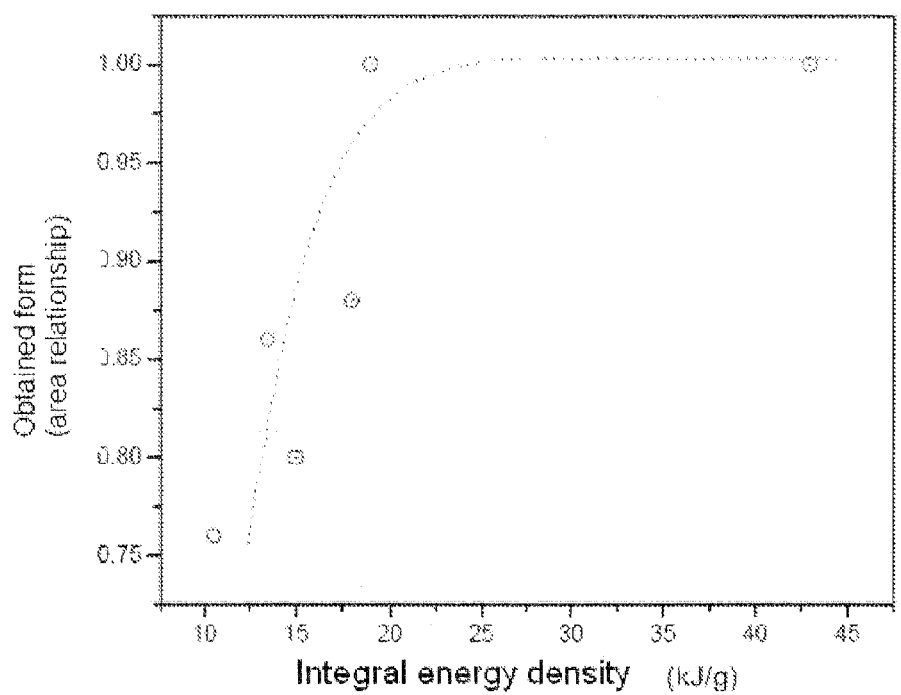

FIG. 10. Characterisation of the different disordered forms of rifaximin obtainable by HEBM depending upon the dose. The different amorphous forms can be identified by the relationship between the area of the halo with high angle divided by the total area (obtained by summing up the area with high angle to the one with low angle).

Figure 11:
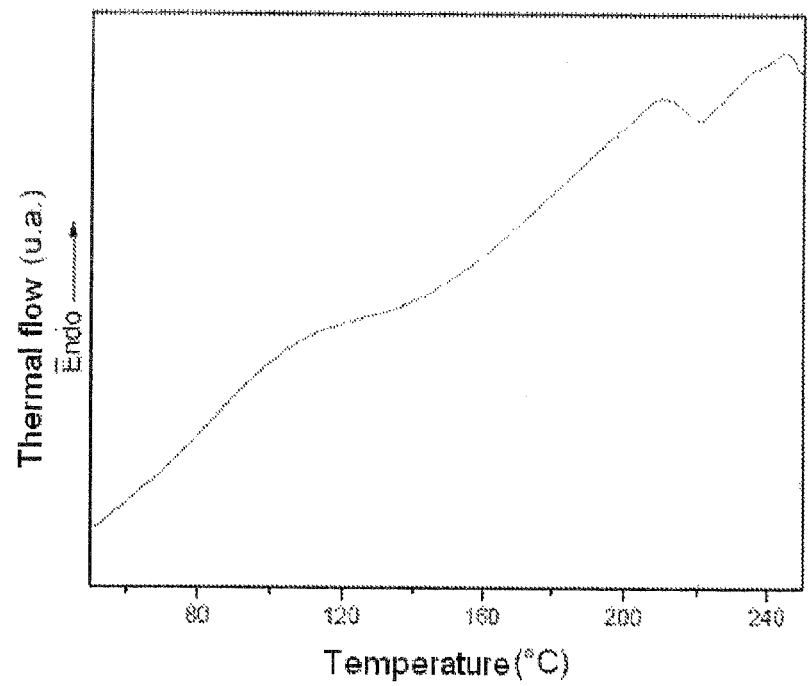

FIG. 11. Scanning differential thermal analysis (DSC) of the amorphous form of rifaximin obtained by means of the method described in the example 8.

Figure 12:
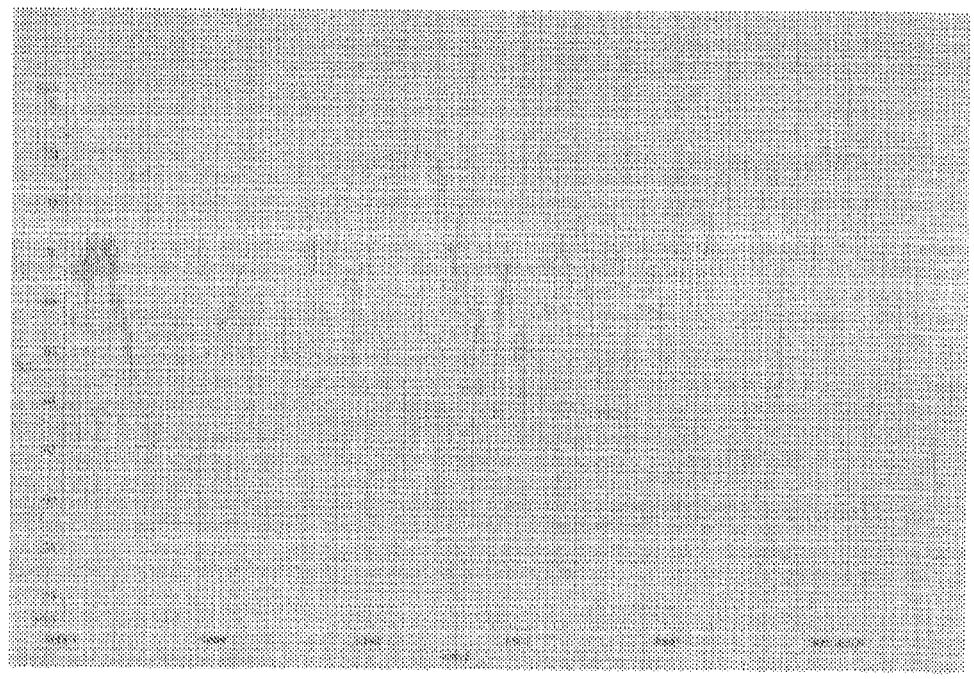

FIG. 12. Fourier Transform Infrared Spectroscopy Spectrum (FTIR) of the amorphous form of rifaximin obtained by means of the method described in the example 3. Identical spectra are obtained even by the amorphous forms of the examples 1, 2, 4, 5, 6, 7, 8, 13.

Figure 13:
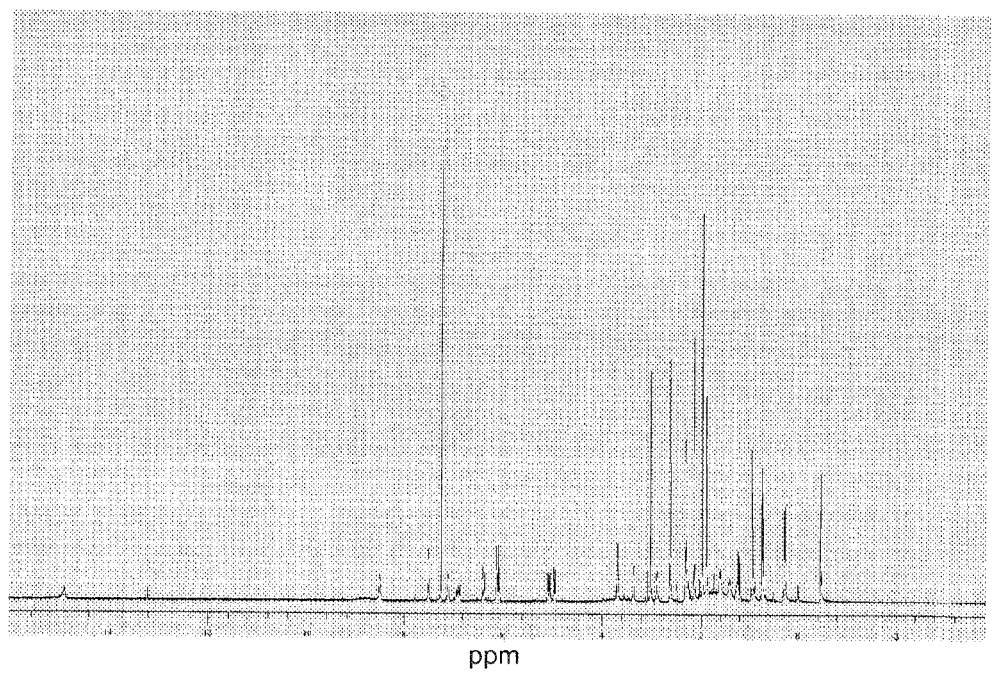

FIG. 13. $^1$H Nuclear magnetic resonance spectrum (NMR) of the amorphous form of rifaximin obtained by means of the method described in the example 3. Identical spectra are obtained even by the amorphous forms of the examples 1, 2, 4, 5, 6, 7, 8, 13

Figure 14:
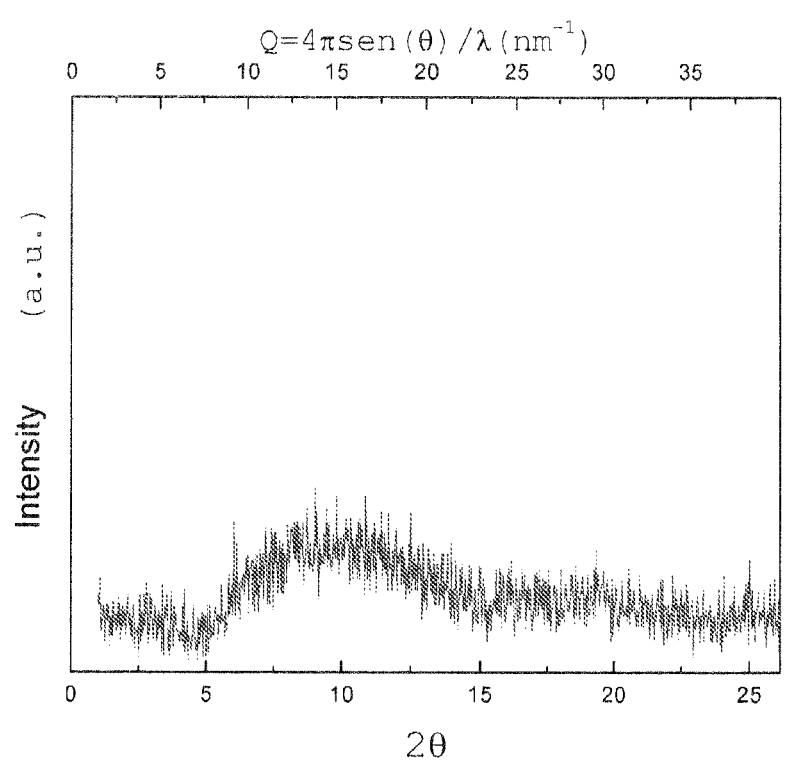

FIG. 14. X-ray diffraction spectrum (XRD) of the amorphous form of rifaximin obtained by means of the method described in the example 13. A single halo in the range 7.7-23.2 $nm^{-1}$ with maximum positioned at $\approx$13.9 $nm^{-1}$ in Q units is pointed out.

Figure 15:
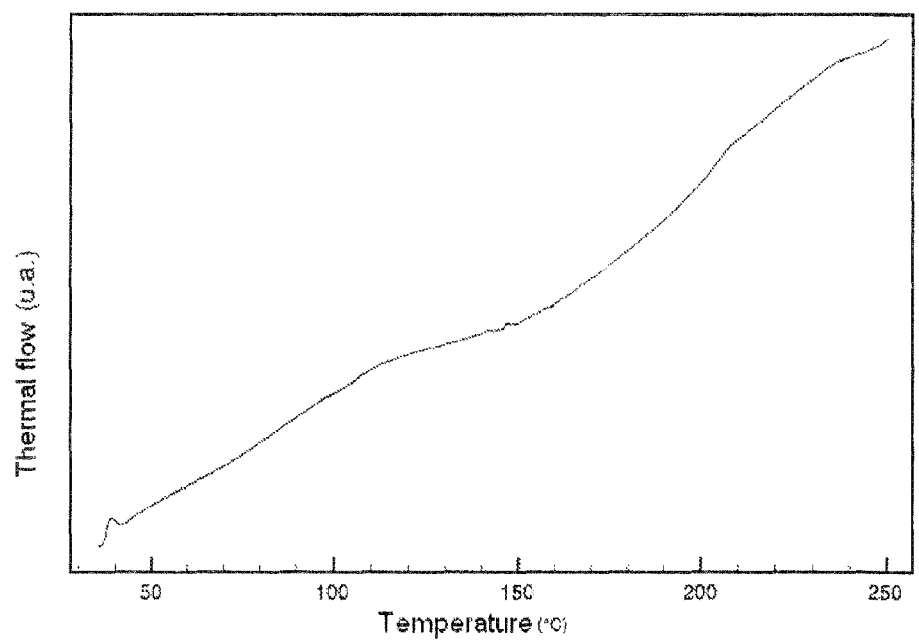

FIG. 15. Scanning differential thermal analysis (DSC) of the amorphous form of rifaximin obtained by means of the method described in the example 13.

Figure 16:
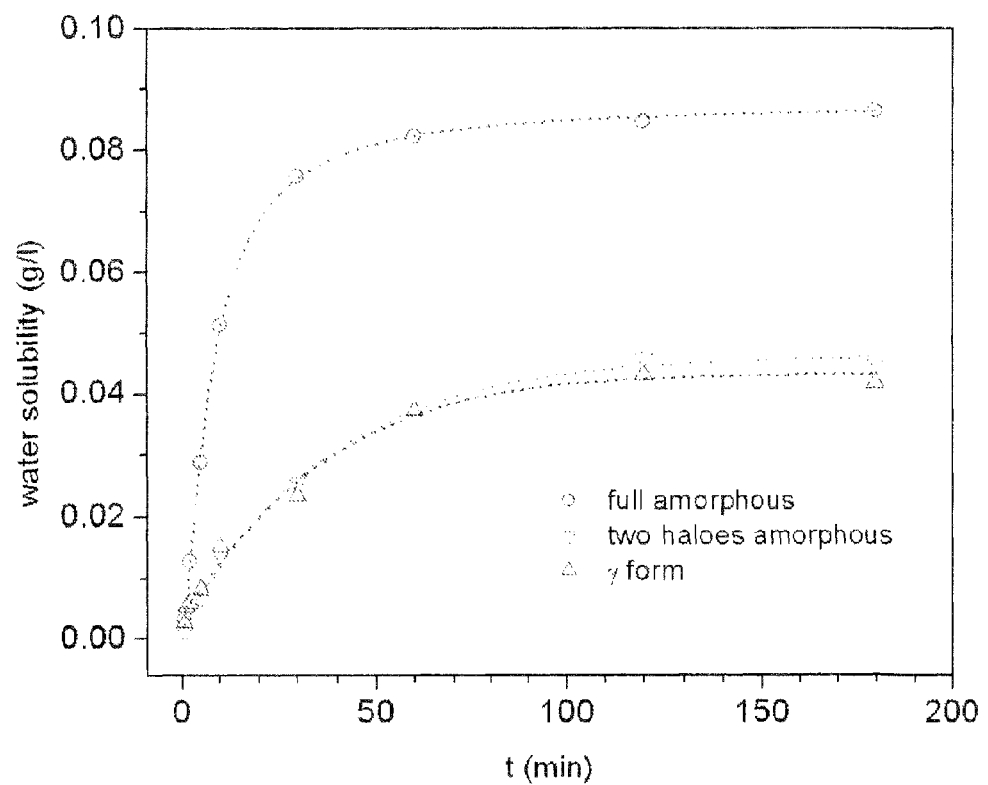

FIG. 16. Graph comparing the solubility at 25° C. depending upon the time of the new amorphous form (obtained according to the example 8) with the amorphous form with two halos (obtained according to the example 1) with the form γ of rifaximin (available on the market). The data are also reported in table 1.

DETAILED DESCRIPTION OF THE INVENTION

The object of the present invention is a a new amorphous form of rifaximin characterized by an X-ray diffraction spectrum showing an X-ray single diffraction halo in the range 7.7-23.2 $nm^{-1}$ in Q units with a maximum positioned in the range 11.3-16.5+/−0.25 $nm^{-1}$ in Q units and absence of peaks proper to crystalline forms.

The new amorphous form has been characterized by the inventors by different techniques such as calorimetry (DSC), X-ray diffractometry (XRD), infrared spectrometry (IR) and Nuclear Magnetic Resonance (NMR) and kinetics of solubility in water. In particular the XRD measures have been performed in apparatus with angular scanning θ-2θ (Siemens D500), by using $MoK_{\alpha 1}$ monochromatic radiation. All samples have been examined in plane sample holders equipped with hollow housing for powders.

The rifaximin in the new amorphous form object of the present invention is characterized by an X-ray diffractogramme, as shown in FIG. 8, 9 or 14, having a single big diffraction halo, characteristic of a disordered structure and the absence of typical diffraction peaks characteristic of the crystalline arrangement. By using the scattering vector Q=4πsenθ/λ (invariant with respect to the wavelength of the used radiation), the diffraction spectra point out that the single halo falls within range 7.7-23.2 $nm^{-1}$ in Q units and it shows a maximum positioned in the range 11.3-16.5+/−0.25 $nm^{-1}$ in Q units and absence of peaks proper to crystalline forms.

The infrared spectra (IR) and the Nuclear Magnetic Resonance spectra (NMR) of rifaximin, shown in FIG. 13 and FIG. 14, respectively, do not show differences with respect to the spectra of the starting material used in the compound preparation, indicating the chemical stability of the product at the end of the process.

In literature the use of compounds belonging to the class of rifamixins is widely reported, in particular of rifaximin as antibiotic. The object of the present invention is the amorphous form of rifamixin described above for use as medicament.

The medicament constituted by the amorphous form of rifaximin of the present invention could be formulated in pharmaceutical compositions suitable to the administration.

Such pharmaceutical compositions could obviously comprise one or more carrier, diluents and/or excipients. For example, they could comprise excipients such as those reported in the main world pharmacopeias such as the European, American or Japanese pharmacopeia.

The compositions could be in any form considered suitable by the person skilled in the art such as for example solid forms, half-solid forms, granular forms and suspensions. The pharmaceutical compositions herein described could be suitable for the oral administration such as for example bare or coated tablets, capsules, packets, pills, powders, granules or for the rectal or topic administration.

An object of the present invention is also a method for high-energy milling for preparing the rifaximin in amorphous form as described hereinafter. The method has the following advantages with respect to the known art:

The High Energy Ball Milling used method is wholly characterized in its process parameters and controllable in the produced effects;

the method is with low environmental impact, falling in the activity field of "Green Chemistry", the use of chemical solvents not being necessary;

the amorphous forms obtained according to the present invention can be selected depending upon simple (energy and/or time) process parameters and it is possible obtaining exactly a specifically wished amorphous form;

the amorphous forms of pharmaceutically active compounds have a higher pharmacological activity than the corresponding compound in a not amorphous form;

the method allows obtaining stable amorphous forms in a short time. In particular, the new amorphous form with a signal diffraction halo shows sensibly higher solubilities than the amorphous forms known up to now.

In the current pharmaceutical technology the treatment of active principles in form of powder is frequently used to obtain materials in micronized form. The main, even if not exclusive, purpose of such treatment is to produce specific wide surfaces in the shorter possible time. However, the treatment of active principles in powder by means of mechanical activations with high energy, and that is with density of energy transferred on the products in powder so as to induce processes for transforming the form of the compound state, is not currently in use in the current pharmaceutical technologies, due to the difficulties in obtaining specific product forms by means of these treatments. With treatments by means of high energy mechanical activations, in fact, not only the objective is different, being the treatment's own aim to obtain structural transformations, but the mode and the energy transfer duration assume specific importance.

Differently from the current milling and/or micronization pharmaceutical technologies, in the processes of "High Energy Milling" the action of mechanical activation is obtained by means of repeated treatments of the single particles with high density transfers by impact. In case of amorphisation processes, which generally request low activation energy, the mechano-chemical process can be characterized by defining an integral density of transferred energy $E_i$ obtainable by integrating on the whole treatment time the power transferred from the milling bodies to the powders. Such definition is also called Dose and defined with the symbol $D_m$. In case of mills with marbles the integral density of energy $E_i$ can be obtained according to the following relationship:

$$E_i = D_m = \eta N_b \cdot v_b E_b t / m_b$$

wherein:

$\eta$ is a coefficient of their own performance of the used apparatuses and of the specific use conditions. Under low filling conditions of the jar reported in the present invention, relatively to the mills with marbles, such coefficient is equal to the unit;

$N_b$ is the number of used marbles;

$v_b$ is the frequency of the impacts of the single marbles against the jar walls so that the product $N_b v_b$ represents the total frequency of the impacts during the treatment;

$E_b$ is the kinetic energy owned by the single marbles at the impact time;

t is the time therefor the treatment is prolonged;

$m_p$ is the mass of product in powder treated mechano-chemically.

The starting product could be obtained by means of synthesis methodologies known to the person skilled in the art or alternatively it could be purchased. For example powder of rifaximin suitable to the invention method can be obtained according to what described in the patents IT 1154655 or EP0161534.

As starting material both structurally not characterized compounds, for example generally purified and undifferentiated, and compounds in specific partially amorphous or crystalline forms or a mixture thereof could be used. The starting product could have a different purity level which could be chosen based upon the purity level of the wished end product.

Subsequently, the method object of the present invention provides a step of subjecting the powder to a plurality of mechanical impacts with one or more milling bodies, so as to transmit thereto an integral energy density of at least 5 kJ/g suitable to make the compound assuming an amorphous state. Preferably the transmitted dose is substantially comprised between 5 and 200 kJ/g, for example 10, 25, 50, 75, 100, 150 kJ/g at room temperature. The process can also be performed at temperatures lower than the environmental one and in such case the dose to be transferred can result to be different from the one pointed out at room temperature.

In the present description under the term milling body each member suitable to transfer energy to the powders is defined. Examples of milling bodies are marbles, rings, cylinders, bars.

The milling bodies, to this purpose, preferably are manufactured in material including metal, or an alloy thereof, or an oxide thereof, even in mixture therebetween for example steel, alumina, zirconia, zirconia stabilized with yttria. Advantageously the energy transmitted with each impact is substantially comprised between 0.1 and 200 mJ, for example 1, 10, 25, 50, 75, 100, 150 mJ.

Preferably, the value of the weight relationship between powder quantity of the compound and of the milling bodies advantageously will be comprised between about 1:1 to 1:50.

The step of subjecting the powder to mechanical impacts preferably takes place in a jar, or mechano-chemical reactor, apt to transmit motion action to the milling bodies contained inside thereof. The jar can be properly cooled from outside. The milling bodies generally are moved from the jar, but they can even be set in motion with other systems (such as for example rotating paddles or other). Therefore, the method object of the present invention comprises a subsequent step of setting in action the jar, after having deposited inside thereof the powder of the compound to make amorphous. The jar action, based upon the speed assumed thereby, induces the motion of the milling bodies and consequently the generation of mechanical impacts on the powder which remains trapped in the impact body-wall of the jar.

According to a preferred form, the method object of the present invention consists in placing in an apparatus of High Energy Ball Milling (HEBM) type a powder quantity of a compound chosen in the group formed by rifaximin, rifamicyn SV, rifampicyn, rifapentine together with steel marbles or other material with weight relationship between the powder quantity of the compound and of the marbles preferably comprised between 1:1 to 1:50.

The mechano-chemical reactors of (HEBM) type generally consist in mills working with high energies, under chemical-physical-mechanical conditions so as to allow the control and monitoring of the main process parameters, for example rotation speed, temperature, rotation time. The compounds to be treated, for example reagents or active principles, are placed at the solid state and in powder in the jars, generally manufactured in steel, together with a certain number of the milling bodies, for example marbles made of steel or other material).

The jars are closed and in case inert atmosphere can be input. Then, they are subjected to the action of the mill which causes, under due conditions, repeated launches of the marbles against the walls of the jar itself. The powder trapped in the impact is able to absorb the whole kinetic energy of the launched marbles, by subjecting not only particulate fracture, but even the formation of new interfaces, cool meltings, atomic/molecular diffusion with formation of new polymorphous phases, electronic rearrangement at the interfaces with formation of new chemical compounds.

Preferably a powder/marbles mass relationship in the order of 1:10 is used, but depending upon the effects which are desired as predominant, such relation can vary.

The filling level of the jar in relation to the total useful volume preferably is in the order of 0.1-0.5, but it can vary even towards lower or higher values, with different effects upon the process efficiency.

The jar then is set in motion by means of an apparatus and the powder is then subjected to the action of high energy milling. Preferably, as it will be detailed hereinafter in some embodiment examples shown by way of example and not with limitative purpose, the method object of the present invention provides placing the jar at a rotational speed substantially comprised between 50 and 2000 revolutions/minute.

In case the motion is imposed by an oscillating motion, the oscillation frequency preferably will be comprised between 10 and 2000 cycles/minute, for example 100, 150, 200, 300, 350, 500, 700 cycles/minute.

The treatment is performed for a time variable depending upon the energy transferred by impact and the total frequency of the impacts. Advantageously the jar could be set in rotation for a time substantially comprised between 1 and 180 minutes, for example 1, 10, 20, 25, 40, 50, 100, 150 minutes. Some representative and not limiting examples are shown in the specific section.

At the end of the method the jar is extracted from the apparatus and the powder in amorphous form is recovered. In FIG. 1 the schemes of some apparatuses currently used for the processes of HEBM type are shown by way of example and not for limitative purpose.

Apart from the HEBM technologies there are other different milling technologies, such as for example those using the so-called "attritors", often simply mechano-reactors with null launch marbles, or those using other impact mechanisms, such as for example the "Ring Mills" (RM) or the "Hammer Mills" (HM), each one characterized by different efficiency and effectiveness levels with respect to the looked-for mechano-chemical action.

The geometry of a ZOZ Symoloyer mill consists in a jar with cylindrical shape and volume higher than or equal to 2 liters. The marbles fill-up the jar for a maximum volume not higher than 50% of the total volume. Therein, a rotor, set in rotation at speeds even higher than 1000 revolutions per minute, imposes to the marbles a free motion (cataracting motion) and the subsequent impact against the walls.

The invention method can be performed at different temperatures, for example any temperature comprised in the range between $-50$ e$+100°$ C.; advantageously it can be performed at room temperature.

In an embodiment of the milling method described above the rifaximin powder, used as starting material, advantageously prior to the milling process itself is mixed with an excipient to increase the solid tendency to transform into the amorphous state, preferably said excipient is amorphous silicon.

An object of the present invention is also a spray-drying method in an atomizer for preparing rifaximin in amorphous form as described hereinafter.

The method comprises a passage wherein a rifaximin solution is subjected to a spray-drying treatment in an atomizer.

The method, by overcoming the mentioned problems of the known art, involves numerous and evident advantages such as obtaining stable rifaximin in amorphous form in a short time, without adding additional substances co-precipitating with rifaximin and with a very high yield. The Spray Drying technology further inserts easily in the current pharmaceutical technologies.

Rifaximin solutions suitable to be used in the method according to the invention are prepared by solubilizing rifaximin powder obtained by means of synthesis methodologies known to the person skilled in the art, for example according to what described in the patents IT 1154655 or EP0161534 or alternatively by purchasing said powder. The powder could be used both in a structurally not characterized form, for example generally purified and undifferentiated in specific amorphous or crystalline forms or in a mixture thereof.

The powder can be solubilized in organic solvents such as methanol, ethanol, ethyl acetate, chloroform, benzene, methylene chloride, dimethylformamide or a mixture thereof.

The rifaximin concentration in the solutions preferably will be comprised in the range of 1-30% w/v (weight/volume), for example 5%, 7%, 10%, 15%, 20%, 25% w/v.

The drying process by means of Spray Drier can be schematized in the following phases:

1) Preparation: the product to be dried is prepared in liquid form as previously described.

2) Atomization: the prepared liquid is sprayed in small drops thanks to a nozzle or to a nozzle or a rotary atomizer. The nozzles use the pressure or the compression of a gas (for example air or nitrogen) to spray the liquid prepared while a disk atomizer uses a a disk rotating at high speed. The speed of air and/or the inert gases depends upon the section of the spray drier. This operation takes place in the drying Chamber (the solid final size mainly depends upon the diameter of the drops produced by the atomizer).

3) Drying: the produced drops are dried by hot air circulating the drying chamber. The heated gas is put in contact with the small drops by using a gas spreader, thus by guiding the liquid evaporation (the contact between the nebulized drops and the hot air causes a rapid evaporation of the solvent, rapidity which is determined by the very high contact area between the drops and the hot air). The gas temperature inside the spraying chamber is comprised between 30-90° C.

4) Recovery: the powder is recovered from the outletting gas by using a Cyclone or a filter (bag filter).

The solution spraying preferably is made to take place with a spraying flow rate per single nozzle: 0.5-20 ml/sec, in a preferred embodiment of the invention at 0.14 ml/s.

Comparative Test of Solubility in Water of Different Amorphous Forms of Rifaximin The solubility in water of different forms of rifaximin was evaluated by means of spectrophotometric method, by performing the analyses on a Lambda10 (Perkin Elmer) apparatus. The tests were performed at room temperature in demineralized water according to the following methodology. 1 g of commercial rifaximin (identified as form γ by X diffractometry) was dried in thermogravimetric apparatus at 105° C. until constant weight. 50.3 mg of the dried powder were weighed and brought in solution with deionized water in 2-L calibrated flask (solution 1). Under these conditions rifaximin was fully dissolved. On a portion of the obtained solution the spectral scanning was performed in the range of wavelengths comprised between 190 and 800 nm, by using as white deionized water. The obtained absorption spectrum points out an isolated maximum at 450.50 nm and such wavelength was used for the analytical measures. The calibration straight line was obtained by dilution of portions of the solution 1, thus obtaining the solution 2 (dilution 1:2.5), the solution 3 (1:10), the solution 4 (1:20) and the solution 5 (1:50). The straight line resulted to follow the Lambert-Beer law, showing linearity in the concentration range of the five measured reference solutions.

For the tests for comparing the solubilities of the different forms, the absorbance of samples obtained from rifaximin suspensions in water excess subjected to constant stirring at 25° C. was measured. After drying at 105° C. until weight constancy, quantities properly weighed of the samples under examination (for a value of about 15 mg) were placed in becker under magnetic stirring, at 25° C. with 80 ml of deionized water. Measures on different samples obtained according to the methodologies reported in the examples 8 and 13 (defined full amorphous), on amorphous ones obtained as described in the examples 1 and 5 (with two halos) and compared to those of commercially available rifaximin, verified as form γ. In different periods of time comprised between 0.5 and 180 minutes, about 2-ml collections were performed, placed in test tube, having the prudence of preventing the collection of the suspended solid by means of filtration with filters for HPLC with porosity 0.2 μm. 0.3 ml of the collected solution were read at the UV by measuring the absorbance 450.50 nm. The samples with higher concentration, with absorbances so as to fall out of the range of the calibration straight line, were diluted until going back to the calibration range. Each experimental point consisted in 3 measures, the values thereof, coincident within 5% of error, were mediated. The results of the experiments described above are summarized in table 1, shown hereinafter. The concentrations are expressed in grams/liter. FIG. 16 shows the solubility versus time of contact with water for the full amorphous samples (obtained according to what reported in the examples 8 and 13), amorphous with two halos (obtained according to what reported in the examples 1 and 5) and of the (commercially acquired) form γ.

TABLE 1

| | Solubility in water (g/l) | | | | |
|---|---|---|---|---|---|
| | Full amorphous (one halo amorphous) | | Amorphous with two halos (two halos amorphous) | | |
| Time (min) | sample from example Nr. 8 | sample from example 13 | sample from example 1 | sample from example 5 | form γ commercial sample |
| 0.5 | 0.0033 | — | 0.00111 | — | 0.0027 |
| 1 | — | — | — | — | 0.0054 |
| 2 | 0.013 | — | 0.0051 | — | 0.0059 |
| 5 | 0.029 | 0.031 | 0.0069 | 0.0071 | 0.0082 |
| 10 | 0.051 | 0.055 | 0.014 | 0.015 | 0.015 |
| 30 | 0.076 | 0.072 | 0.025 | 0.027 | 0.023 |
| 60 | 0.082 | 0.081 | 0.036 | 0.037 | 0.037 |
| 120 | 0.085 | 0.086 | 0.046 | 0.044 | 0.043 |
| 180 | 0.0864 | 0.089 | 0.045 | 0.046 | 0.042 |

The experimental data reported herein, related to the solubility variation in time, show that the kinetics of solubility in demineralized water at 25° C. of the different amorphous forms of rifaximin are very different therebetween. In particular, the evident difference is between the so-called amorphous forms of rifaximin showing two diffraction halos (prepared as reported in the examples 1 and 5 and even described in the International patent application WO2009/108730) and the amorphous form of rifaximin defined by us as "full—amorphous" (prepared as described in the examples 8 and 13). The full amorphous form, in fact, has a better kinetics of dissolution in water and a higher solubility. The greater solubility of the full-amorphous rifaximin product is an advantage for all pharmacological applications wherein a high solubility value enhances the bioavailability of the drug itself as widely demonstrated by the existing scientific and patent literature. The data of solubility in water point out that the discovery of an unexpected rifaximin in amorphous form makes it possible obtaining a product solubility in water well above what known up to now. The invention is described in details hereinafter in the following examples which have the purely illustrative purpose, without limiting the scope of the conferred protection.

EXAMPLES

Example 1

0.7 grams of rifaximin are placed in powder into a jar of the free volume of 40 $cm^3$ and added with 2 12-mm-wide steel marbles (unitary mass 7.12 grams). The jar is closed and made integral to an apparatus of "shaker" type, actuated at about 900 revolutions/minute, equal to a frequency of impacts of about 60 impacts per second. Under optimum conditions the obtained energy transfer is in the order of 90-100 mJ per impact. The time length of the mechano-chemical action is equal to 15 minutes. The recovered material has amorphous structure and shows the XRD pattern shown in FIG. 2.

Example 2

0.5 grams of rifaximin are placed in powder into a jar of the free volume of 40 $cm^3$ and added with 4 8-mm-wide marbles of zirconium oxide ($ZrO_2$) (unitary mass 1.63 grams). The jar is closed and made integral to an apparatus of "shaker" type, actuated at about 900 revolutions/minute, equal to an impact frequency of about 120 impacts per second. Under optimum conditions the obtained energy transfer is in the order of 20-25 mJ per impact. The time length of the mechano-chemical action is equal to 60 minutes. The recovered material has amorphous structure and shows the XRD pattern shown in FIG. 3.

Example 3

1 gram of rifaximin is placed in powder into a jar of the free volume of 40 cm$^3$ and added with 4 10-mm-wide marbles of zirconia ($ZrO_2$) (unitary mass 3.06 grams). The jar is closed and made integral to an apparatus of "shaker" type, actuated at about 900 revolutions/minute, equal to an impact frequency of about 120 impacts per second. Under optimum conditions the obtained energy transfer is in the order of 40-50 mJ per impact. The time length of the mechano-chemical action is equal to 60 minutes. The recovered material has amorphous structure and shows the XRD pattern shown in FIG. 4.

Example 4

5 grams of rifaximin are placed in powder into a jar of Ring Mill type, as reported in caption of FIG. 1. The jar is closed with special cover and made integral to the apparatus which transfers thereto roto-oscillating motions, with consequent rolling mixed action+impact of the bodies inside the jar. The action is prolonged for 30 minutes. The time length of the mechano-chemical action is equal to 30 minutes. The recovered material has amorphous structure and shows the XRD pattern shown in FIG. 5.

Example 5

3 grams of rifaximin are placed in powder into a jar of planet type (see caption in FIG. 1) and added with 35 6-mm-wide steel marbles (unitary mass 0.89 grams). The jar is closed and made integral with an apparatus of planet type, actuated at 300 revolutions/minute, equal to an impact frequency of about 175 impacts per second. Under used conditions the obtained energy transfer is about 5-10 mJ per impact. The time length of the mechano-chemical action is equal to 60 minutes. The recovered material has amorphous structure and shows the XRD pattern shown in FIG. 6.

Example 6

0.5 grams of rifaximin are placed in powder into a jar of the free volume of 40 cm$^3$ and added with 40 steel marbles with a diameter of 3 mm (unitary mass 0.13 grams). The jar is closed and made integral to an apparatus of "shaker" type, actuated at about 900 revolutions/minute, equal to an impact frequency of about 1200 impacts per second. Under optimum conditions the obtained energy transfer is in the order of 1-3 mJ per impact. The time length of the mechano-chemical action is equal to 60 minutes. The recovered material has amorphous structure and shows the XRD pattern shown in FIG. 7.

Example 7

1 gram of rifaximin is placed in powder into a jar of the free volume of 40 cm$^3$ and added with 4 10-mm-wide zirconia marbles ($ZrO_2$) (unitary mass 3.06 grams). The jar is closed and made integral to an apparatus of "shaker" type, actuated at about 900 revolutions/minute, equal to an impact frequency of about 120 impacts per second. Under optimum conditions the obtained energy transfer is in the order of 40-50 mJ per impact. The time length of the mechano-chemical action is equal to 120 minutes. The recovered material has amorphous structure, with first absent halo, and shows the XRD pattern shown in FIG. 8.

Example 8

1.1 grams of rifaximin are placed in powder within an egg-like jar (see caption in FIG. 1) and added with 6 12-mm-wide steel marbles (unitary mass 7.12 grams). The jar is closed and made integral with an apparatus of "shaker" type, actuated at about 900 revolutions/minute, equal to an impact frequency of about 180 impacts per second. Under optimum conditions the obtained energy transfer is in the order of 90-100 mJ per impact. The time length of the mechano-chemical action is equal to 60 minutes. The recovered material has amorphous structure with first absent halo and shows the XRD pattern shown in FIG. 9.

Example 9

By means of "Profile fitting analysis" it is possible characterizing the rifaximin forms obtained according to the present invention by means of the quantification of the relationship of the integral areas of the two halos (with low and high angular range) characterizing the diffraction spectrum of the obtained disordered structures. By defining a relationship of areas R equal to $$R=Area(7,7<Q<23,2)/(Area(7,7<Q<23,2)+Area(3,5<Q<7,2))$$

it is possible having a characterisation of the produced material. The types of the produced material, then, can be easily put in correlation with process parameters. In particular, all selected examples being able to promote the transformation, the total energy transferred to the powder during the whole treatment per mass unit (dose or integral energy density), easily obtainable the total impact frequency and the energy per single impact being known, can be used as reference parameter. FIG. 10 points out the correlation between the obtained form and the integral energy density.

Example 10

Scanning Differential Thermal Analysis (DSC)

7.2 mg of amorphous rifaximin obtained according to what reported in the example 8 are placed in an aluminium sample holder sealed by pressing in die with a sample cover, made in aluminium too. The sealed sample holder was then pierced with a pin point. The so-obtained sample holder was placed in the measurement housing of a scanning differential calorimeter (Perkin Elmer DSC7) and put in argon flow for 10 minutes (30 cc/min). As thermal reference an empty sample holder, obtained in a way analogous to the measurement sample holder, was used. Subsequently, the sample was heated from 50 to 250° C. with scanning speed equal to 20° C./min.

Example 11

NMR Spectrum

1H NMR spectra were registered with a BRUCKER AC 400 MHz spectrometer by using CDCl3 deuterated chloroform as solvent and tetramethylxylan (TMS) as inner standard. No variation among the compounds obtained in the examples is observed compared to the reference spectra (initial rifaximin).

Example 12

FTIR Spectrum

IR spectra were registered with a FTIR Spectrum 1000 Perkin Elmer spectrometer by using KBr pellets. No variation among the compounds obtained in the examples is observed compared to the reference spectra (initial rifaximin).

Example 13

10 g of rifaximin are dissolved in dichlorometane and brought to volume of 100 ml. The so-obtained solution is placed in a Spray Dryer apparatus and atomized on a nozzle with a flow rate of 0.14 ml/s. Input air is inlet into the apparatus in countercurrent with flow rate equal to 70 m$^3$/h and temperature kept constant at 55° C. Rifaximin powder condensation having the features described as in the following samples 14 to 15.

Example 14

A sample carrier made of plastic material with a cavity with cylindrical shape with diameter equal to about 2.5 cm and depth equal to 2 mm intended for the sample housing is filled-up by light manual compression with rifaximin obtained as from the example 1 and it is subjected to analysis by X-ray diffraction. The used apparatus is of teta-2teta type, equipped with upstream monochromator. The used radiation is Mo $K_{\alpha 1}$. An X-ray diffraction spectrum as shown in FIG. 15 is obtained.

Example 15

DSC Analysis (Scanning Thermal Differentiation)

6.6 mg of amorphous rifaximin obtained according to what reported in the example 1 are placed in a aluminium sample holder sealed by pressing in die with a sample cover, made in aluminium too. The sealed sample holder was then pierced with a pin point. The so-obtained sample holder was placed in the measurement housing of a scanning differential calorimeter and put in argon flow for 10 minutes (30 cc/min). As thermal reference an empty sample holder, obtained in a way analogous to the measurement sample holder, was used. Subsequently the sample was heated from 50 to 250° C. with scanning speed equal to 20° C./min. The DSC spectrum is shown in FIG. 16.

BIBLIOGRAPHY

1. EP1676848B1 Polymorphous forms of rifaximin as antibiotics
2. US2009/0082558A1 Amorphous form of rifaximin and processes for its preparation
3. WO/2008/155728 PROCESS FOR PREPARING AMORPHOUS RIFAXIMIN AND THE AMORPHOUS RIFAXIMIN THUS OBTAINED
4. IT1154655 DERIVATI IMIDAZO-RIFAMICINICI METODI PER LA LORO PREPARAZIONE E LORO USO COME SOSTANZA AD AZIONE ANTIBATTERICA
5. EP0161534 NEW PROCESS FOR THE SYNTHESIS OF PYRIDO-IMIDAZO-REFAMYCINS
6. WO2009/108730 Forms of Rifaximin and uses thereof.

The invention claimed is:

1. Rifaximin in amorphous form characterized by an X-ray diffraction spectrum showing a single diffraction halo in the range 7.7-23.2 nm$^{-1}$ in Q units with a maximum positioned in the range 11.3-16.5±0.25 nm$^{-1}$ in Q units and absence of peaks indicative of crystalline forms.

2. Rifaximin in amorphous form according to claim 1 further characterized by an X-ray diffraction spectrum substantially identical to that in FIG. 8.

3. Rifaximin in amorphous form according to claim 1 further characterized by an X-ray diffraction spectrum substantially identical to that in FIG. 9.

4. Rifaximin in amorphous form according to claim 1 further characterized by an X-ray diffraction spectrum substantially identical to that in FIG. 14.

5. Pharmaceutical composition comprising rifaximin in amorphous form according to claim 1 and one or more excipients.

6. Method of using a medicament comprising administering a therapeutically effective amount of the pharmaceutical composition described in claim 5.

7. Method for producing rifaximin in amorphous form according to claim 1 comprising:
   a) pre-arranging said rifaximin in form of powder and
   b) subjecting said powder to a plurality of mechanical impacts with one or more milling bodies so that an integral energy density equal to at least 50 kJ/g is transferred, said integral energy density being so as to make said rifaximin assume an amorphous state characterized by an X-ray diffraction spectrum showing a single diffraction halo positioned in the range 7.7-23.2 nm$^{-1}$ in Q units with a maximum positioned in the range 11.3-16.5±0.25 nm$^{-1}$ in Q units and absence of peaks indicative of crystalline forms.

8. Method according to claim 7, wherein said integral energy density is comprised between 90 and 100 kJ/g.

9. Method according to claim 7, wherein rifaximin is mixed with amorphous silica in a).

10. Method according to claim 7, wherein said subjecting said powder to a plurality of mechanical impacts comprises depositing said powder within a reactor of High Energy Ball Milling type, wherein said reactor includes said milling bodies inside thereof.

11. Method according to claim 10, wherein said reactor is set in motion at a speed substantially comprised between 900 and 2000 revolutions per minute and for a period of time substantially comprised between 60 and 180 minutes.

12. Method for producing rifaximin in amorphous form according to claim 1 comprising subjecting a rifaximin solution to a spray-drying treatment in an atomizer by using a nozzle flow rate comprised between 0.5-20 ml/sec and a gas at a temperature of at least 50° C.

13. Method according to claim 12, wherein said rifaximin solution contains methylene chloride.

14. Method according to claim 12, wherein said solution rifaximin is comprised of a concentration in rifaximin between 1-30% w/v.

15. Method according to claim 12, wherein said gas is air.

16. Method according to claim 12, wherein said gas is nitrogen.

* * * * *